United States Patent
Srivastava et al.

(10) Patent No.: US 11,224,201 B1
(45) Date of Patent: Jan. 18, 2022

(54) PET BED

(71) Applicants: Jaya Srivastava, Markham (CA);
Ureta Neshana, Markham (CA)

(72) Inventors: Jaya Srivastava, Markham (CA);
Ureta Neshana, Markham (CA)

( * ) Notice: Subject to any disclaimer, the term of this patent is extended or adjusted under 35 U.S.C. 154(b) by 194 days.

(21) Appl. No.: 16/554,825

(22) Filed: Aug. 29, 2019

(51) Int. Cl.
*A01K 29/00* (2006.01)
*A01K 1/035* (2006.01)
*A61K 41/00* (2020.01)

(52) U.S. Cl.
CPC .......... *A01K 1/0353* (2013.01); *A61K 41/00* (2013.01)

(58) Field of Classification Search
CPC ...... A01K 1/0353; A01K 1/035; A01K 1/015; A01K 1/0157; A61G 7/065; A47D 15/001
See application file for complete search history.

(56) References Cited

U.S. PATENT DOCUMENTS

| | | |
|---|---|---|
| 4,008,688 A | 2/1977 | Nicholas |
| 5,784,995 A * | 7/1998 | Willinger ............ A01K 1/0353 119/28.5 |
| 6,173,675 B1 * | 1/2001 | Licciardo ............ A01K 1/0353 119/28.5 |
| 6,305,318 B1 | 10/2001 | Ford |
| 6,557,494 B2 * | 5/2003 | Pontes ................ A01K 15/025 119/702 |
| 6,988,771 B1 * | 1/2006 | Huang .................. A47C 31/00 297/219.1 |
| 7,614,362 B2 * | 11/2009 | Dunn .................. A01K 1/0353 119/28.5 |
| 10,701,895 B1 * | 7/2020 | Cukrov ............... A01K 1/0353 |
| 10,881,080 B2 * | 1/2021 | Komatsubara ....... A01K 1/0353 |
| 2004/0216680 A1 * | 11/2004 | Lamstein ............ A01K 1/0353 119/28.5 |
| 2014/0230735 A1 * | 8/2014 | Coulter .............. A01K 1/0353 119/28.5 |
| 2018/0161226 A1 * | 6/2018 | Von Behren ......... A61G 7/065 |

* cited by examiner

*Primary Examiner* — Trinh T Nguyen
(74) *Attorney, Agent, or Firm* — Sanchelima & Associates, P.A.; Christian Sanchelima; Jesus Sanchelima

(57) ABSTRACT

A pet bed that provides an ideal resting place for pets is disclosed herein. The pet bed comprises a fabric shell and a bed filler contained within the fabric shell. The fabric shell defines a support region and a continuous sidewall emanating therefrom to surround an open center area. The fabric shell is made of organic hemp canvas and the bed filler is made of organic latex. The bed filler comprises a padding made of organic latex. A cushion is removably positioned in the center area of the fabric shell. At least one pocket is disposed on the sidewall of the fabric shell, and a healing crystal is removably inserted within the pocket. As a result, the pet bed spreads positive energy and provides comfort, healing, wellness, happiness and peace of mind to a pet and a pet owner.

10 Claims, 3 Drawing Sheets

PET BED

BACKGROUND OF THE INVENTION

1. Field of the Invention

The present disclosure relates to a pet bed. More particularly, the present disclosure relates to an organic pet bed comprising a healing crystal.

2. Description of the Related Art

Animals by nature like to rest in an environment of comfort, security, and familiarity. In particular, pets such as cats and dogs, like to rest on their owner's lap. In addition to providing comfort, the contour of the owner's lap cradles the pet with a sense of security. However, due to the increasingly busy schedule of their owners, such pets are spending an increasing amount of time alone indoors. Pets left alone could become lonely and anxious. And some pet owners become so attached to their cats and dogs that they suffer guilt when they leave the home.

Many different devices such as pet bed and toys have been developed to keep the pets happy and healthy. Pet beds are developed to provide a comfortable place to pets for resting or sleeping and also acts as a replacement for owner's lap. Typically, such beds include a support portion and a cushioning member disposed above the support member to provide comfort. However, most existing beds comprises a unitary structure that is almost impossible to wash with a conventional household washing machine.

Several devices have been designed in the past. None of them, however, include a pet bed that is capable of addressing the foregoing discussed issues.

Applicant believes that a related reference corresponds to U.S. Pat. No. 6,305,318 filed by Janet J. Ford describes a human shaped pet bed. Janet reference discloses a pet bed comprising a washable outer covering of the shape and texture of a pair of human shorts having disposed within a removable anatomical cushion, and a removable, scented pouch disposed within the outer covering. However, Janet reference lacks to address the depression and other healthy aspects experienced by the pets.

Applicant believes that a related reference corresponds to U.S. Pat. No. 4,008,688 filed by Dimitri P. Nicholas describes a pet bed. Dimitri reference discloses a pet bed having insecticidal properties. The pet bed comprises a powder-impervious bottom sheet formed of box board material and an upper sheet or layer, which is formed of a needled fabric or felt-like material, defining therebetween a pocket or reservoir, which contains a powdered insecticide. When the pet, such as a dog or cat, lies on the upper surface, a small amount of the powdered insecticide is picked up, patted, or rubbed onto the pet's body as it comes into contact with it. This release of the insecticide controls the fleas. However, Dimitri reference also lacks to address the depression and natural comfort experienced by the pets.

Other documents describing the closest subject matter provide for a number of more or less complicated features that fail to solve the problem in an efficient and economical way. None of these patents suggest the novel features of the present invention.

SUMMARY OF THE INVENTION

It is an object of the present invention to provide a pet bed that offers comfort desired by a pet.

It is another object of the present invention to provide a pet bed that enhances positive energy, healing, wellness, happiness and peace of mind for a pet and a pet owner.

It is yet another object of the present invention to provide a pet bed made of organic material.

It is yet another object of the present invention to provide a pet bed comprising a fabric shell and a bed filler contained within the fabric shell, wherein the fabric shell is made of organic hemp canvas, and wherein the bed filler may be made of organic hemp but preferably of organic latex.

It is yet another object of the present invention to provide a pet bed comprising a removable cushion.

It is yet another object of the present invention to provide a pet bed comprising at least one pocket having a healing crystal, wherein the healing crystal is selected from a group consisting of rose quartz, clear quartz, and amethyst.

Further objects of the invention will be brought out in the following part of the specification, wherein detailed description is for the purpose of fully disclosing the invention without placing any limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
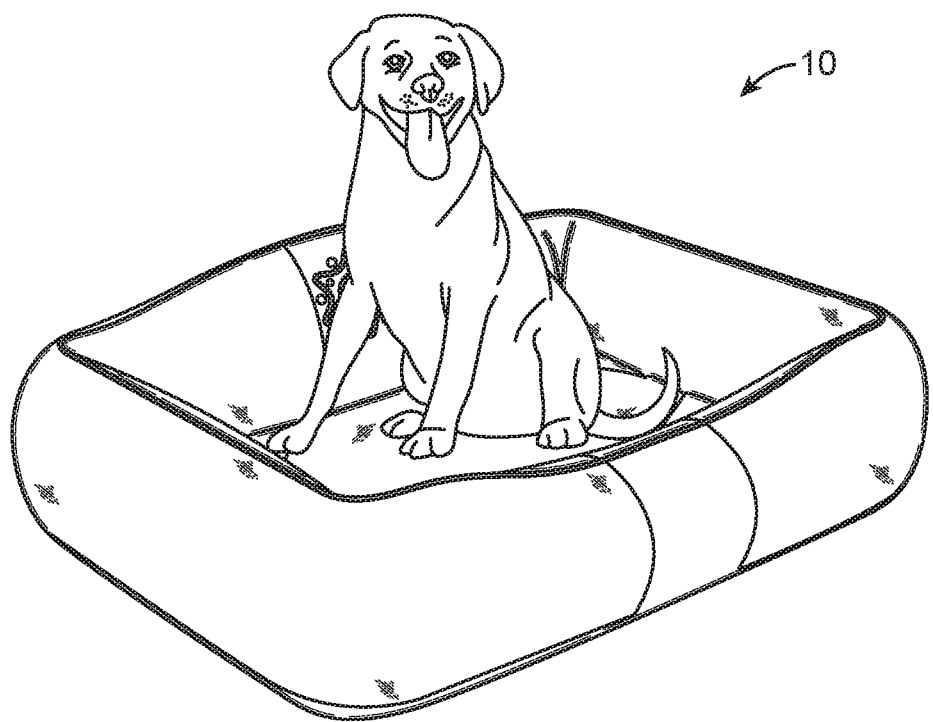
FIG. 1 exemplarily illustrates a pet such as a dog resting on a pet bed 10 according to an embodiment of the present invention.
Figure 2:
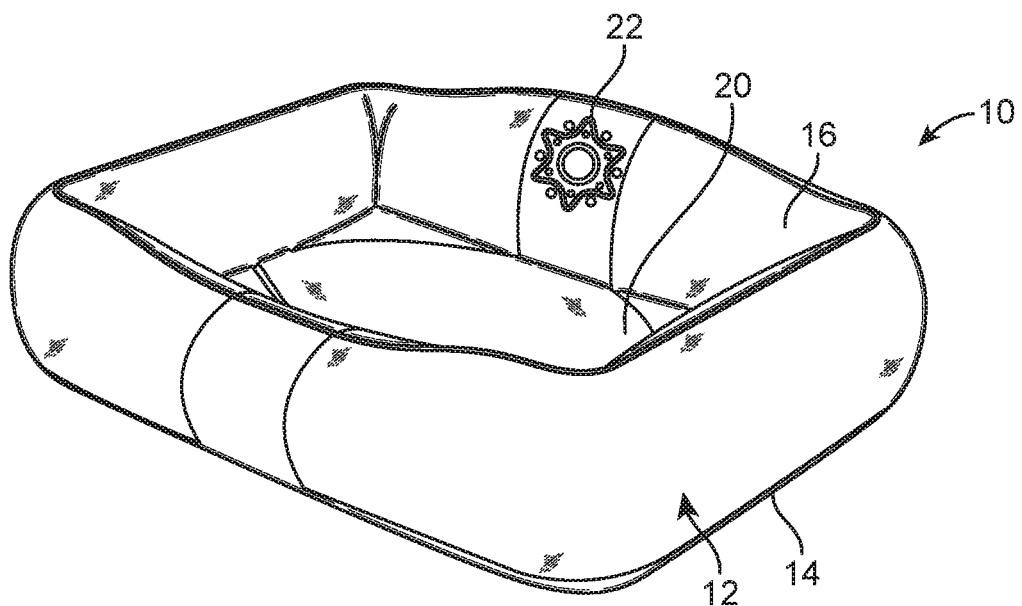
FIG. 2 exemplarily illustrates a perspective view of the pet bed 10 according to an embodiment of the present invention. The pet bed 10 comprising a fabric shell 12, a cushion 20, at least one pocket 22 and a healing crystal 24 is illustrated.
Figure 3:
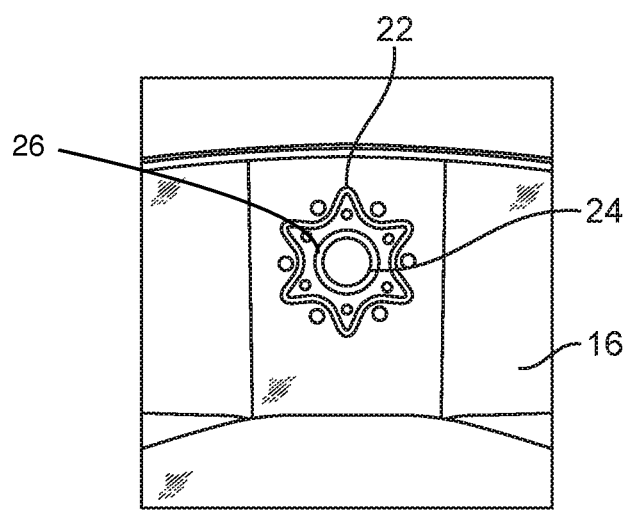
FIG. 3 exemplarily illustrates the healing crystal 24 removably inserted within the at least one pocket 22 of the pet bed 10 according to an embodiment of the present invention.
Figure 4:
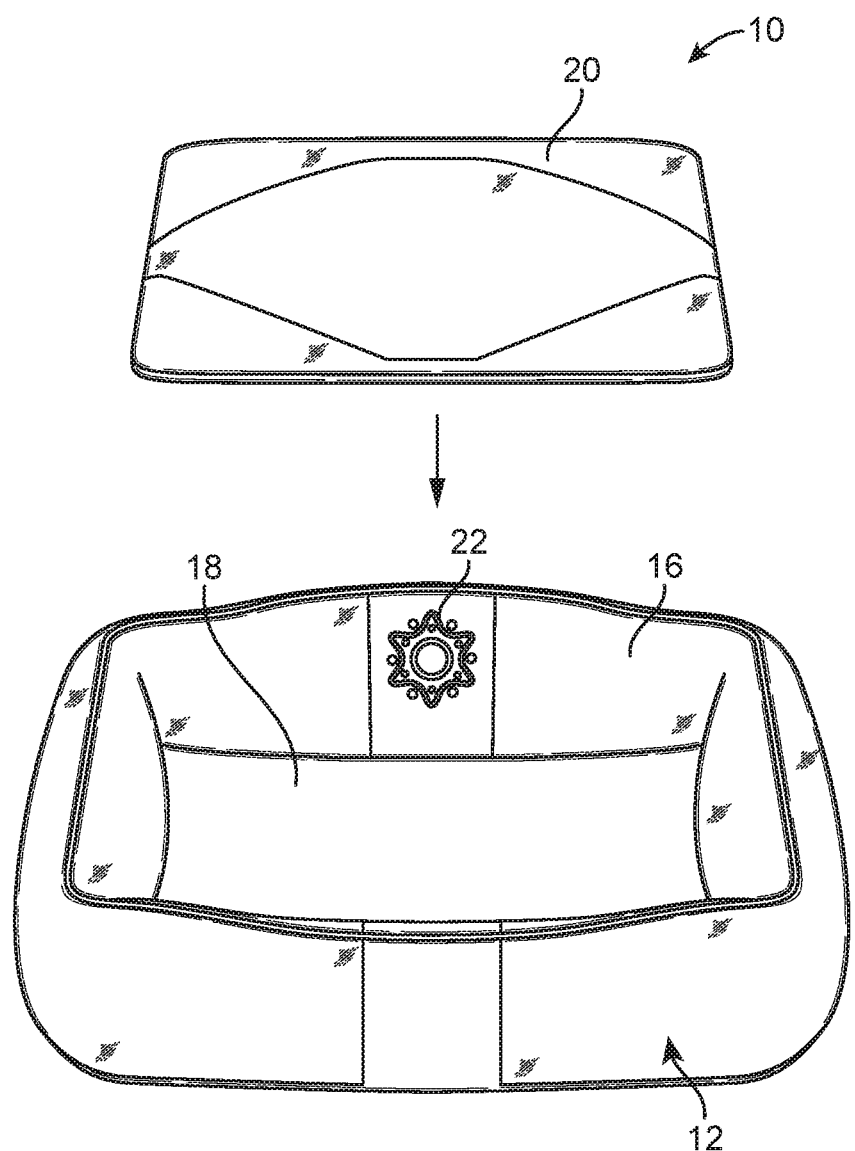
FIG. 4 exemplarily illustrates an exploded view of the fabric shell 10 and the cushion 20 according to an embodiment of the present invention.

Referring now to the drawings, FIGS. 1-4, where the present invention is generally referred with numeral 10, it can be observed that a pet bed 10 is disclosed. The pet bed 10 spreads positive energy and provides comfort, healing, wellness, happiness and peace of mind to a pet and a pet owner.

The pet bed 10 comprises a fabric shell 12 and a bed filler contained within the fabric shell 12. The fabric shell 12 defines a support region 14 and a continuous sidewall 16 emanating therefrom to surround an open center area 18. In one embodiment, the pet bed 10 is can be made of organic material. In one embodiment, the fabric shell 12 is made of organic hemp canvas. In one embodiment, the bed filler can be made of organic hemp or preferably organic latex. The bed filler comprises a padding made of organic latex. Pet bed 10 or fabric shell 12 may be made of organic materials such as hemp, latex or sherpa, for example. The bed filler may be made of the same aforementioned materials.

A cushion 20 is removably positioned in the center area 18. The removable cushion 20 enables easy maintenance for the pet owners. In one embodiment, the cushion 20 could be machine washed. In another embodiment, the cushion 20 is made of machine washable material. The bed filler and the cushion 20 are configured to promote sleep and relaxation to a pet residing in the pet bed 10.

At least one pocket 22 is disposed on the sidewall 16 of the fabric shell 12. A healing crystal 24 is removably inserted within at least one pocket 22. Alternatively, a fragrance packet 26 may be inserted into at least one pocket 22. The healing crystal 24 is infused with positive vibrations before insertion into the pocket 22. In one embodiment, the healing crystal 24 is selected from a group including, but not limited to, rose quartz, clear quartz and amethyst. In one embodiment, the crystal 24 are selected based on the need of the pets. The present invention offers healing energy of crystals 24 along with natural and organic material, such as hemp, latex or Sherpa, for true comfort. In one embodiment, at least one pocket 22 could be a cork. In one embodiment, essential oil is provided in the cork to provide aromatherapy, which enhances aroma of the pet bed.

In one embodiment, the pet bed 10 comprises width 1033 mm, height 300 mm and depth 780 mm. In another embodiment, the pet bed 10 is rectangular in shape. In yet another embodiment, the pet bed 10 is in circular shape, oval shape, or any other geometrical shape. In yet another embodiment, the dimension, color, material, density of the pet bed 10 may vary according to the preference of the pet owners.

Advantageously, the present invention is extremely simple to use requiring minimal manipulation for assembly and disassembly. The pet bed 10 is ideally suited for all pets, particularly dogs and cats. The pet bed 10 offers maximum comfort for the pet animal. The pet bed 10 made of organic material and the healing crystal 24 that enhances positive energy, comfort, healing, wellness, happiness and peace of mind for the pet animal and pet owner. Further, the present invention provides a unique, blissful experience for any pet animal. The pet bed 10 is suitable for anyone who wants to provide an ideal resting place for their pet.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A system for a pet bed, comprising:
  a. a fabric shell defining a support region and a continuous sidewall emanating therefrom to surround an open center area, said continuous sidewall includes four walls, each wall of said four walls includes an outer side and an inner side, said inner side and said outer side have a rounded shape, a middle portion of the inner side of each of the four walls having protruding towards the open center area said continuous sidewall includes a top ridged portion connecting a top portion of the inner side of each wall of the four walls with a top portion of the outer side of each wall of the four walls;
  b. a bed filler contained within the fabric shell;
  c. a cushion removably positioned within the open center area, wherein said fabric shell, said bed filler, and said cushion is made from an organic material, said cushion is flat having a rectangular shape to fit in a bottom of said fabric shell, said cushion is made of a machine washable material;
  d. at least one pocket disposed on the sidewall of the fabric shell comprising a healing crystal and a fragrance packet therein, said at least one pocket is made of a cork material including essential oil to provide aromatherapy, said at least one pocket is located on a rectangular portion, the rectangular portion is located on the middle portion of at least one of the four walls, said at least one pocket has a shape of a star having concavities, a circle portion is located between the cavities; and
  e. at least one healing crystal is located on the center of the pocket.

2. The pet bed of claim 1, wherein the fabric shell is made of organic hemp canvas.

3. The pet bed of claim 1, wherein the bed filler is made of organic latex.

4. The pet bed of claim 1, wherein the bed filler comprises a padding made of organic latex.

5. The pet bed of claim 1, wherein the bed filler is made of sherpa.

6. The pet bed of claim 1, wherein the healing crystal is rose quartz.

7. The pet bed of claim 1, wherein the healing crystal is clear quartz.

8. The pet bed of claim 1, wherein the healing crystal is amethyst.

9. The pet bed of claim 1, wherein said pocket includes essential oil to provide aromatherapy.

10. A system for a pet bed, consisting of:
  a. a fabric shell defining a support region and a continuous sidewall emanating therefrom to surround an open center area, said continuous sidewall includes four walls, each wall of said four walls includes an outer side and an inner side, said inner side and said outer side have a rounded shape, a middle portion of the inner side of each of the four walls having protruding towards the open center area, said continuous sidewall includes a top ridged portion connecting a top portion of the inner side of each wall of the four walls with a top portion of the outer side of each wall of the four walls, said fabric shell is made of organic hemp canvas;
  b. a bed filler contained within the fabric shell, said bed filler is made of organic latex;
  c. a cushion removably positioned within the open center area, wherein said fabric shell, said bed filler, and said cushion is made from an organic material, said cushion is flat having a rectangular shape to fit in a bottom of said fabric shell, said cushion is made of a machine washable material to enable easy maintenance;
  d. at least one pocket disposed on the sidewall of the fabric shell comprising a healing crystal and a fragrance packet therein, said healing crystal is a rose quartz;
  e. at least one pocket is made of a cork material, the cork includes essential oil to provide aromatherapy, said at least one pocket is located on a rectangular portion, the rectangular portion is located on the middle portion of one of the four walls, said at least one pocket has a shape of a star having concavities, a circle portion is located between the cavities; and
  f. at least one healing crystal is located on the center of the pocket.

\* \* \* \* \*